(12) United States Patent
Fouts et al.

(10) Patent No.: US 9,131,832 B2
(45) Date of Patent: Sep. 15, 2015

(54) CANNULA ARRANGEMENT FOR MINIMALLY INVASIVE SURGERY

(71) Applicants: Brian Fouts, San Martin, CA (US);
Daniel E. Cooper, Dallas, TX (US)

(72) Inventors: Brian Fouts, San Martin, CA (US);
Daniel E. Cooper, Dallas, TX (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 13/966,882

(22) Filed: Aug. 14, 2013

(65) Prior Publication Data
US 2014/0051928 A1   Feb. 20, 2014

Related U.S. Application Data

(60) Provisional application No. 61/683,432, filed on Aug. 15, 2012.

(51) Int. Cl.
*A61B 1/04* (2006.01)
*A61B 1/00* (2006.01)
*A61B 1/018* (2006.01)

(52) U.S. Cl.
CPC ............. *A61B 1/00154* (2013.01); *A61B 1/018* (2013.01)

(58) Field of Classification Search
CPC ..... A61B 1/313; A61B 1/3132; A61B 1/0154
USPC ................. 600/114, 128; 604/164.09, 164.11
See application file for complete search history.

(56) References Cited

U.S. PATENT DOCUMENTS

| | | | |
|---|---|---|---|
| 4,808,156 A * | 2/1989 | Dean | 604/43 |
| 5,171,245 A | 12/1992 | Cezana | |
| 5,395,317 A | 3/1995 | Kambin | |
| 5,456,673 A | 10/1995 | Ziegler et al. | |
| 5,762,629 A | 6/1998 | Kambin | |
| 6,454,783 B1 | 9/2002 | Piskun | |
| 7,066,879 B2 | 6/2006 | Fowler et al. | |
| 7,249,602 B1 | 7/2007 | Emanuel | |
| 7,344,547 B2 | 3/2008 | Piskun | |
| 8,061,359 B2 | 11/2011 | Emanuel | |
| 8,096,941 B2 | 1/2012 | Fowler et al. | |

(Continued)

OTHER PUBLICATIONS

Covidien—P-navel systems: pictures and description published on the internet before Sep. 2, 2010 (2 pages).

(Continued)

*Primary Examiner* — Anhtuan T Nguyen
*Assistant Examiner* — Timothy J Neal
(74) *Attorney, Agent, or Firm* — Flynn, Thiel, Boutell & Tanis, P.C.

(57) ABSTRACT

An arrangement for surgery including a hub and a cannula assembly connected thereto. The cannula assembly defines a first fully enclosed chamber extending substantially along a length of the cannula assembly, with the first fully enclosed chamber being coextensive with a head central passage of the hub such that a first tool is configured to extend through the hub and the first fully enclosed chamber. The cannula assembly defining a second fully enclosed chamber that extends along only a portion of the length of the cannula assembly and spaced from the hub. The second fully enclosed chamber having an entrance and an exit being spaced from the hub for allowing a second surgical tool to extend through the second fully enclosed chamber without also passing through the hub or the first fully enclosed chamber. The first fully enclosed chamber and the second fully enclosed chamber being substantially parallel.

12 Claims, 11 Drawing Sheets

(56) References Cited

U.S. PATENT DOCUMENTS

| | | |
|---|---|---|
| 8,257,254 B2 | 9/2012 | Piskun |
| 8,394,018 B2 | 3/2013 | Piskun |
| 2004/0066008 A1* | 4/2004 | Smith .................. 277/628 |
| 2007/0032701 A1 | 2/2007 | Fowler et al. |
| 2007/0282266 A1 | 12/2007 | Davidson |
| 2008/0027476 A1 | 1/2008 | Piskun |
| 2008/0058588 A1 | 3/2008 | Emanuel |
| 2008/0058842 A1 | 3/2008 | Emanuel |
| 2008/0275483 A1* | 11/2008 | Makower et al. .......... 606/192 |
| 2009/0012530 A1 | 1/2009 | Fowler |
| 2009/0030274 A1* | 1/2009 | Goldfarb et al. .......... 600/106 |
| 2010/0081875 A1 | 4/2010 | Fowler et al. |
| 2010/0130826 A1 | 5/2010 | Piskun |
| 2010/0137691 A1 | 6/2010 | Piskun |
| 2012/0158015 A1 | 6/2012 | Fowler et al. |

OTHER PUBLICATIONS

Covidien—SILS Port: pictures and description published on the internet before Sep. 2, 2010 (2 pages).

Advanced Surgical Devices—TriPort and QuadPort devices: pictures and description published on the internet before Sep. 2, 2010 (1 page).

Endo Ethicon—Single Site Laparoscopy Device: pictures and description published on the internet before Sep. 2, 2010 (1 page).

* cited by examiner

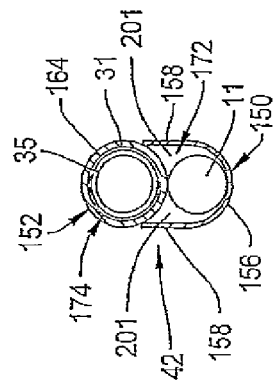
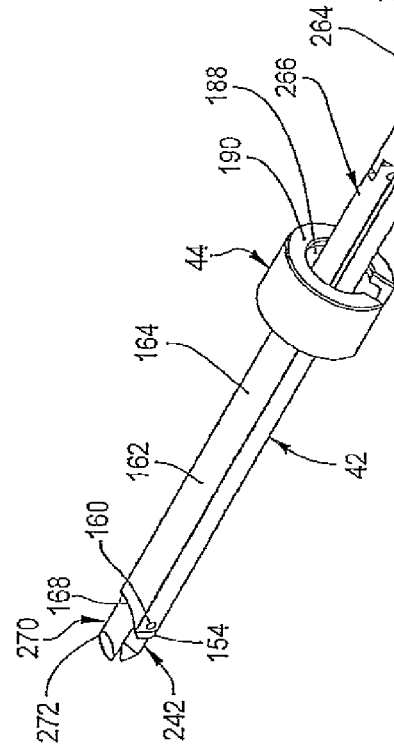
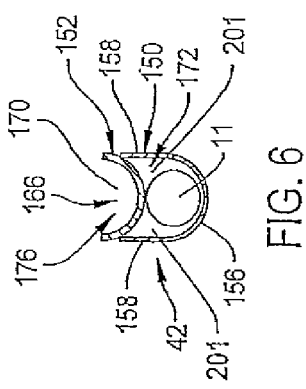

CANNULA ARRANGEMENT FOR MINIMALLY INVASIVE SURGERY

CROSS REFERENCE TO RELATED APPLICATION

This application claims the benefit of U.S. Provisional Application No. 61/683,432, filed Aug. 15, 2012, the disclosure of which is hereby incorporated by reference in its entirety.

FIELD OF THE INVENTION

The present invention relates to an arrangement for performing endoscopic surgery in conjunction with multiple surgical instruments, one of which may include an imaging apparatus, such as an endoscope.

BACKGROUND OF THE INVENTION

Endoscopy is a minimally invasive surgical procedure which utilizes imaging apparatus for the purpose of providing a view of an interior portion of the body, without requiring that a large surgical opening be made in the patient to gain access to the surgical site. An endoscope is one type of such imaging apparatus which is placed in the body at the location at which it is necessary to perform a surgical procedure. Along with the endoscope, other types of surgical tools or instruments may be placed in the body at the surgical site so as to carry out a particular procedure. Examples of such instruments are cutting instruments, such as shaver-type devices which mechanically cut bone and soft tissue, or radio-frequency (RF) probes which are used to remove tissue via ablation or to coagulate tissue to minimize bleeding at the surgical site, to name only a few. In an endoscopic procedure, the surgeon views the surgical site through the endoscope in order to manipulate the other surgical instrument or instruments so as to perform the desired surgical procedure.

The development of endoscopes and their companion surgical instruments has made it possible to perform minimally invasive surgery that requires only small openings to be made in the patient, which openings are called portals. One advantage of performing endoscopic surgery is the reduction of the number of incisions made in the patient and/or the reduction of incision size, which reduces healing time after surgery. Still another advantage of endoscopic surgery is that it exposes less of the interior tissue of the patient's body to the open environment. This minimal opening of the patient's body lessens the extent to which the internal tissue and organs are open to infection.

In traditional endoscopic surgery, the endoscope and the surgical instrument are introduced to the surgical site through separate small portals, and once inside the patient, the instrument and endoscope must be correctly spatially oriented relative to one another through triangulation. Specifically, the surgeon must place the working end, typically the distal end, of the surgical instrument within the field of view of the endoscope so that the surgical instrument can be correctly manipulated, and must continually maintain this correct spatial relationship between the endoscope and the instrument throughout the surgical procedure. Since the surgical instrument and endoscope are inserted into the patient at varying angles and from separate locations, maintaining the correct spatial relationship between the two devices can be taxing on the surgeon. Further, during multiple-portal endoscopic surgery, surgical instruments, such as the blade of a surgical shaver or an RF probe, may collide with the endoscope optics, which can damage the endoscope and/or potentially cause a delay in surgery. Additionally, it can be difficult for surgeons to maintain the proper location of the endoscope within the surgical site during surgery.

While endoscopic surgery has been very successful in carrying out various surgical procedures, the medical field continually strives to lessen trauma caused to the patient during an endoscopic surgical procedure. For example, the number of portals created in the patient during knee arthroscopy has been reduced from three portals to two portals by expanding the functionality of the endoscope itself and of other surgical instruments to eliminate the need for a dedicated outflow portal. Further, the present trend in endoscopic procedures is to perform all necessary surgical functions through a single portal. One of the challenges presented by single-port surgical procedures is preventing stretching and/or tearing of the incision defining the single portal as the surgical instruments are manipulated and levered relative to the patient while the same extend into the patient through the portal.

SUMMARY OF THE INVENTION

In view of the above, one object of the invention is to require the formation of only a small, single incision in the patient during endoscopic surgery by maintaining the various surgical instruments and the endoscope in the correct spatial orientation relative to one another to effectively prevent undesirable deviation of these tools during surgery. A further object is to allow ready positioning of the surgical instrument relative to the endoscope so that the surgical instrument is inserted into the patient directly into the field of view of the endoscope.

In this regard, the present invention includes an access and positioning arrangement which is intended for placement or positioning adjacent the skin of the patient where the incision or portal is located and through which portal the surgical site is accessed. The arrangement according to the invention thus acts an exterior access point to the surgical site which effectively defines multiple pathways leading thereto through a single incision defined within the patient. The arrangement includes a pair of channels which are sidewardly-spaced from one another and which communicate with the surgical site via the portal defined in the patient. Respective surgical instruments or tools are inserted into the respective channels for extension into the surgical site through the portal, which channels serve to maintain the instruments in a predefined and fixedly-spaced relation with one another.

BRIEF DESCRIPTION OF THE DRAWINGS

FIG. 6 is a cross-sectional view of the surgical tool arrangement of the invention taken along line VI-VI of FIG. 1, without including any internal details of the endoscope.

FIG. 7 is a cross-sectional view of the surgical tool arrangement of the invention taken along line VII-VII of FIG. 1, without including any internal details of the endoscope or the surgical instrument.

FIG. 11 is a rear perspective view of the access and positioning arrangement of the invention having a trocar and an obturator located therein.

Figure 1:
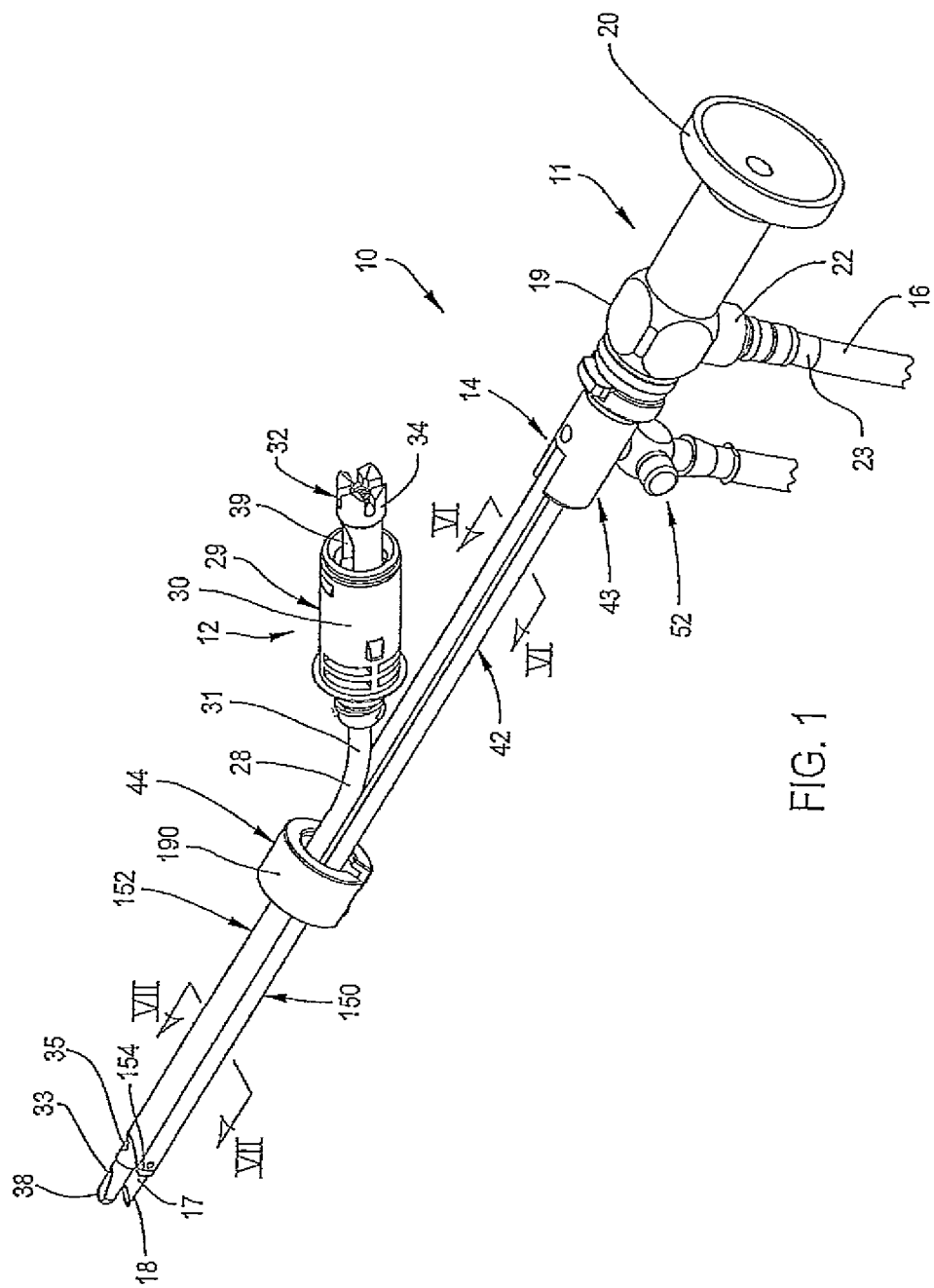
FIG. 1 is an illustration of a surgical tool arrangement for use in an endoscopic surgical procedure which incorporates an access and positioning arrangement according to a first embodiment of the invention, and illustrating examples of two types of surgical instruments usable therewith.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined herein. Hence, specific dimensions and other physical characteristics relating to the embodiments disclosed herein are not to be considered as limiting, unless expressly stated otherwise.

FIG. 1 illustrates a surgical tool arrangement 10 for carrying out a surgical procedure, such as an endoscopic procedure. One specific endoscopic procedure in which the surgical tool arrangement 10 may be utilized is an arthroscopic procedure wherein examination and/or treatment of damage of the interior of a joint, such as the knee, wrist, or shoulder, is carried out. The surgical tool arrangement 10 according to an aspect of the invention may be used to carry out an endoscopic procedure utilizing a limited number of incisions, and preferably a single incision or port defined in the patient. The surgical tool arrangement 10 generally includes an endoscope 11, a surgical instrument 12, and an access and positioning arrangement 14. As discussed in further detail below, the endoscope 11 and the surgical instrument 12 are assembled to the access and positioning arrangement 14 for the purpose of carrying out an endoscopic procedure.

The endoscope 11 (FIG. 2) is conventional and will accordingly only be briefly described herein. The endoscope 11 includes a transmission cable 16 and a console or light source (not shown). The endoscope 11 is defined by an elongated and generally hollow shaft 17 with a distal end 18 configured for insertion within a body cavity and located within and extending through the access and positioning arrangement 14. The endoscope 11 has a proximal end 19 which mounts thereon an eyepiece 20 configured to provide a viewing port through which the surgeon views the surgical field, for example, through connection between the viewing port, a digital camera, and a display screen or monitor. A light port 22 is connected to the light source to selectively transmit light to a target at the surgical site via the endoscope 11.

The transmission cable 16 is configured to transmit light from a proximal end (not shown) of the transmission cable 16 associated with the light source to a distal end 23 of the transmission cable 16 attached to the light port 22. In one embodiment, the transmission cable 16 incorporates optical fibers suited to transmit electromagnetic radiation via total internal reflection of such radiation within the fiber material. The proximal end and the distal end 23 of the transmission cable 16 include geometries, such as plugs, conducive to receiving and emitting, respectively, electromagnetic radiation.

The light source selectively provides electromagnetic radiation, such as visible light, for use in the operating theater. In one embodiment, the candlepower of light emitted from the light source is selectively adjustable via a switch. Further, the light source includes a socket to which intermediary devices, such as the transmission cable 16, are connected to transmit light from the light source to instruments such as the endoscope 11.

The endoscope 11 contains a number of internal mechanisms which are not shown here, one of which is an imaging arrangement in the form of an optical train having one or more lenses which transmit an image from the distal end 18 to the eyepiece 20. The hollow shaft 17 of the endoscope 11 incorporates mounting structures which maintain alignment of the components of the optical train toward the eyepiece 20, whereby electromagnetic radiation from the light source may be transmitted into the endoscope 11 via the transmission cable 16 and the light port 22.

It will be appreciated that the endoscope 11 may include, instead of an imaging arrangement embodied by an optical train as mentioned above, a compact imaging device such as a charged-coupled device (CCD) or a metal-oxide-semiconductor (CMOS) arranged at the distal end 18 of the endoscope 11, which is configured to process and/or transmit information received from a lens or a lens assembly located distally therefrom. Instead of directing the otherwise unprocessed light information via an optical train, such information is communicated as a processed signal to a console via a wired connection. It is contemplated that a trocar 62 or an obturator could be used instead of the endoscope 11 (e.g., during insertion of the surgical tool arrangement 10 into a patient) or before the endoscope 11 is used. Such a trocar and obturator are well known to those skilled in the art and are disclosed in U.S. Pat. No. 5,456,673 entitled "LOCKING CANNULA FOR ENDOSCOPIC SURGERY," the entire contents of which are hereby incorporated herein by reference. The trocar 62 is also described below.

Turning now to the surgical instrument 12 (FIG. 1), such surgical instrument 12 may be in the form of a cutting instrument, such as a shaver-type device which mechanically cuts bone and hard tissue, a radio-frequency (RF) probe, or any other type of tissue-manipulating tool. For purposes of illustration, the surgical instrument 12 is a conventional cutter or shaver, and thus will not be described in detail herein. The surgical instrument 12 generally includes an outer housing assembly 29 including a hub 30 and an elongated outer tube 31 fixed to and projecting outwardly from the hub 30. In the illustrated embodiment, the elongated outer tube 31 includes a bend 28 at its proximal end, and a distal end which defines a cutting window 33 therein. The surgical instrument 12 additionally includes a cutting element 32 located within the outer housing assembly 29. The cutting element 32 includes a hub 34 which is configured for engaging with a drive element of a surgical handpiece (not shown here), and an inner cutting tube or drive shaft 35 which is fixed to and projects from the hub 34 and extends within the elongated outer tube 31. A distal end of the cutting tube 35 cooperates with the cutting window 33 of the elongated outer tube 31.

Specifically, in the illustrated embodiment, the distal end of the cutting tube 35 defines therein a cutting window 38 which, upon rotation of the cutting element 32 relative to and within the outer housing assembly 29, effectively cuts or shaves tissue in cooperation with the cutting window 33 of the elongated outer tube 31. Further, the cutting tube 35 defines therein a suction passage which is in communication with a suction port 39 defined in the hub 34. The suction port 39 communicates with a suction arrangement located within the handpiece so that suction can be applied to the surgical site via the surgical instrument 12. As described in more detail below, a trocar or an obturator 26 could be used instead of the cutting element 32 (e.g., during insertion of the surgical tool arrangement 10 into a patient) or before the cutting element 32 is used.

Turning now to the access and positioning arrangement 14, and with reference to FIG. 1, the access and positioning arrangement 14 includes a head or hub 43 at the proximal end thereof, a cannula assembly 42 and a sheath lock 44. The endoscope 11 is inserted into the hub 43 and locks therewith as described in more detail below. The endoscope 11 extends through the cannula assembly 42 and the distal end 18 of the endoscope 11 projects out of the cannula assembly 42. The surgical instrument 12 also extends through the cannula assembly 42 and the cutting window 33 of the elongated outer tube 31 is located outside of the cannula assembly 42. The sheath lock 44 hinders fluids from exiting a portion of the cannula assembly 42.

In the illustrated example, the hub 43 (FIGS. 3-4) of the access and positioning arrangement 14 connects the endoscope 11 to the access and positioning arrangement 14 and also provides fluid to the cannula assembly 42. The hub 43 includes an upper or proximal head portion 80 and a distal head portion 46 (see FIG. 4). The proximal head portion 80 includes components for connecting the endoscope 11 to the hub 43 and can be identical to the upper head portion of the locking cannula as disclosed in previously-mentioned U.S. Pat. No. 5,456,673 entitled "LOCKING CANNULA FOR ENDOSCOPIC SURGERY". Therefore, the proximal head portion 80 can include a lock unit 90 having a lock carrier 91 made up of an annular pedestal 91A and an annular cap 91B, a generally rectangular slider 110, an O-ring 130, an internal O-ring seal 82, and an upper portion 40 and downward tapered portion 41 of a head central passage 48 identical to the same components in U.S. Pat. No. 5,456,673 and function in the same manner to lock the endoscope 11 to the hub 43. As discussed in more detail below, the endoscope 11 is locked to the hub 43 as the hollow shaft 17 of the endoscope 11 is inserted into a proximal end of the hub 43 and through the head central passage 48 of the hub 43 as disclosed in U.S. Pat. No. 5,456,673.

The illustrated hub 43 includes the distal head portion 46 housing a portion of the cannula assembly 42 and a valve unit 52. The distal head portion 46 of the hub 43 is substantially tubular and includes a distal portion 54 of the head central passage 48 therein. The distal head portion 46 of the hub 43 includes a first section 68 in the middle of the hub 43 and a second section 70 at the distal end of the hub 43. The first section 68 includes a T-shaped fluid path 69 having a cross tube area 71 of the head central passage 48 with a proximal end 73 thereof being aligned with and coextensive with a narrow portion 65 of the head central passage 48 within the proximal head portion 80 and a distal end 75 thereof opening into the second section 70 of the distal head portion 46. The cross tube area 71 of the T-shaped fluid path 69 also has a branch tube 72 extending radially from the cross tube area 71 and housing the valve unit 52 partially therein. The second section 70 of the distal head portion 46 houses a portion of the cannula assembly 42.

Figure 3:
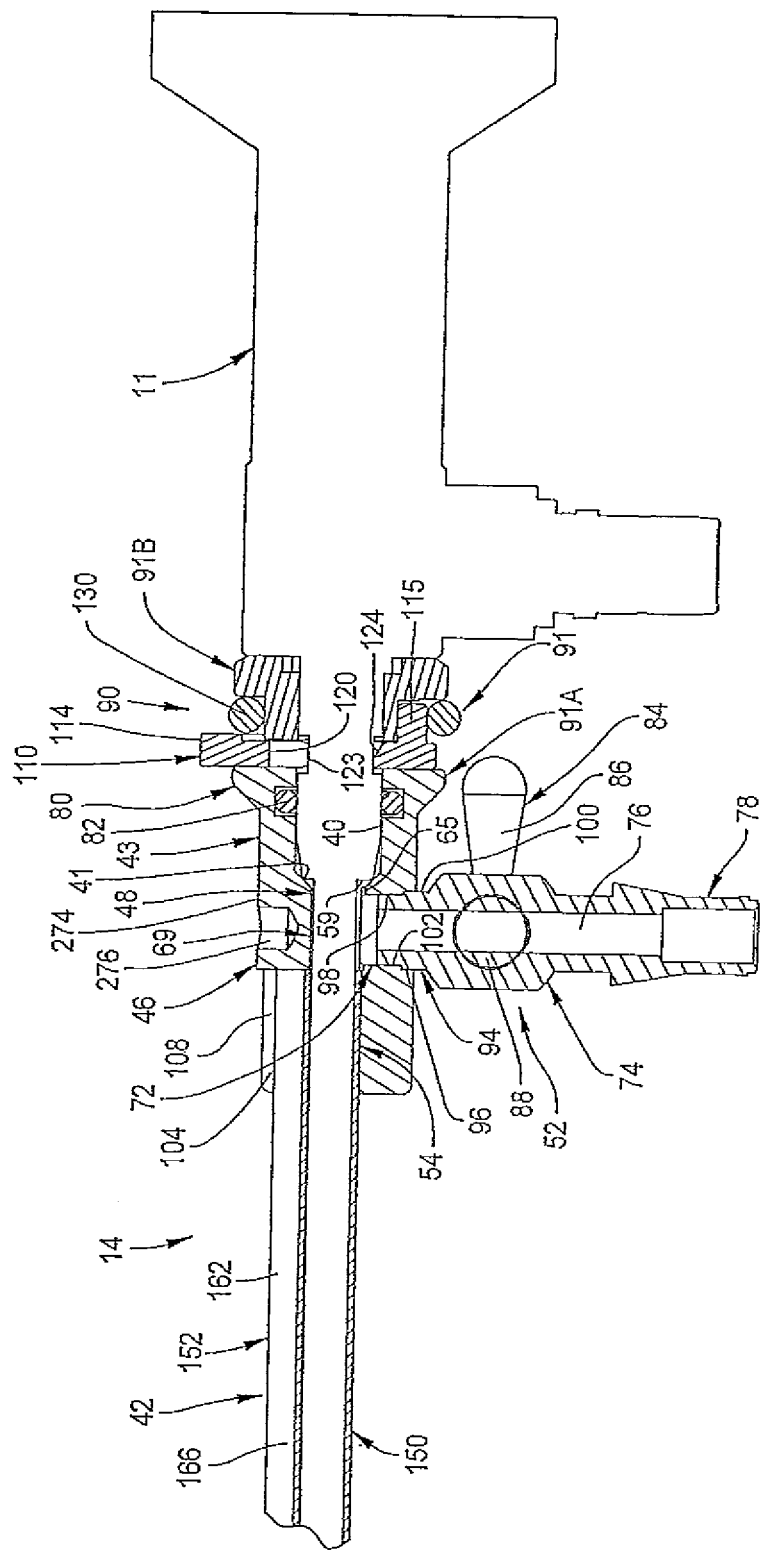
FIG. 3 is a fragmentary cross-sectional view of a hub of the access and positioning arrangement of the invention, without including any internal details of the endoscope.
Figure 4:
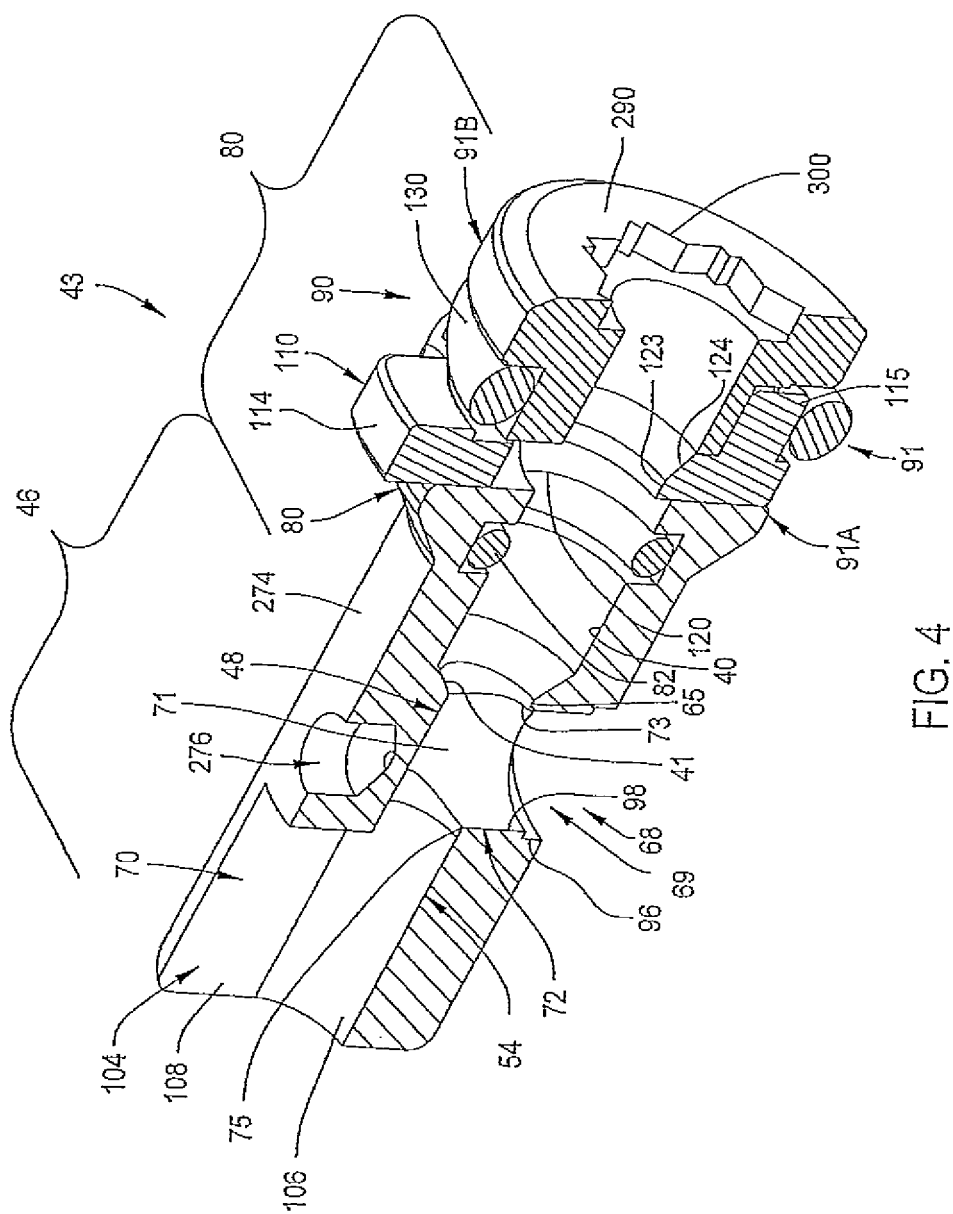
FIG. 4 is a perspective cross-sectional view of a hub of the access and positioning arrangement of the invention.

In the illustrated example, the valve unit 52 includes a valve body 74 having a central fluid path 76 therethrough in fluid communication with the branch tube 72 of the hub 43. The valve unit 52 includes a radially outer end 78 connectable, as through suitable resilient tubing (not shown) to, for example, a conventional inflation gas source, a conventional suction source, or another desired fluid source, such as a source of irrigation liquid. The central fluid path 76 includes a conventional stopcock, or on/off valve, 84. The valve 84 may be of variable opening size to modulate the flow of fluid therethrough. In the embodiment shown, the valve 84 comprises a manually actuable valve handle 86 rotatable to rotate a corresponding rotatable valve element 88 in a conventional manner. A radially inner end 94 of valve body 74 extends into the branch tube 72 of the hub 43. As illustrated in FIGS. 3-4, the branch tube 72 of the hub 43 is stepped and includes an outer annular larger portion 96 and an inner annular smaller portion 98. Likewise, the radially inner end 94 of the valve body 74 includes a corresponding outer tubular larger portion 100 and an inner tubular smaller portion 102. The outer tubular larger portion 100 of the radially inner end 94 of the valve body 74 is positioned within the outer annular larger portion 96 of the branch tube 72 of the hub 43 and the inner tubular smaller portion 102 of the radially inner end 94 of the valve body 74 is positioned within the inner annular smaller portion 98 of the branch tube 72 of the hub 43 to connect the valve unit 52 to the hub 43. The valve unit 52 can be fixedly connected to the hub 43 via welding, an adhesive, an interference fit or any other connection scheme. It is contemplated that other valve units having other on/off valves could be used.

The illustrated distal head portion 46 of the hub 43 houses a portion of the cannula assembly 42 and allows the cannula assembly 42 to fluidly communicate with the head central passage 48. As illustrated in FIGS. 3 and 4, the distal head portion 46 of the hub 43 includes a U-shaped slot 104 opening radially outward defining a centrally located arcuate wall 106 and a pair of parallel upper walls 108. The cross tube area 71 of the head central passage 48 of the first section 68 of the distal head portion 46 of the hub 43 opens into an area within the centrally located arcuate wall 106 of the U-shaped slot 104. The cannula assembly 42 fits within the U-shaped slot 104.

Figure 5:
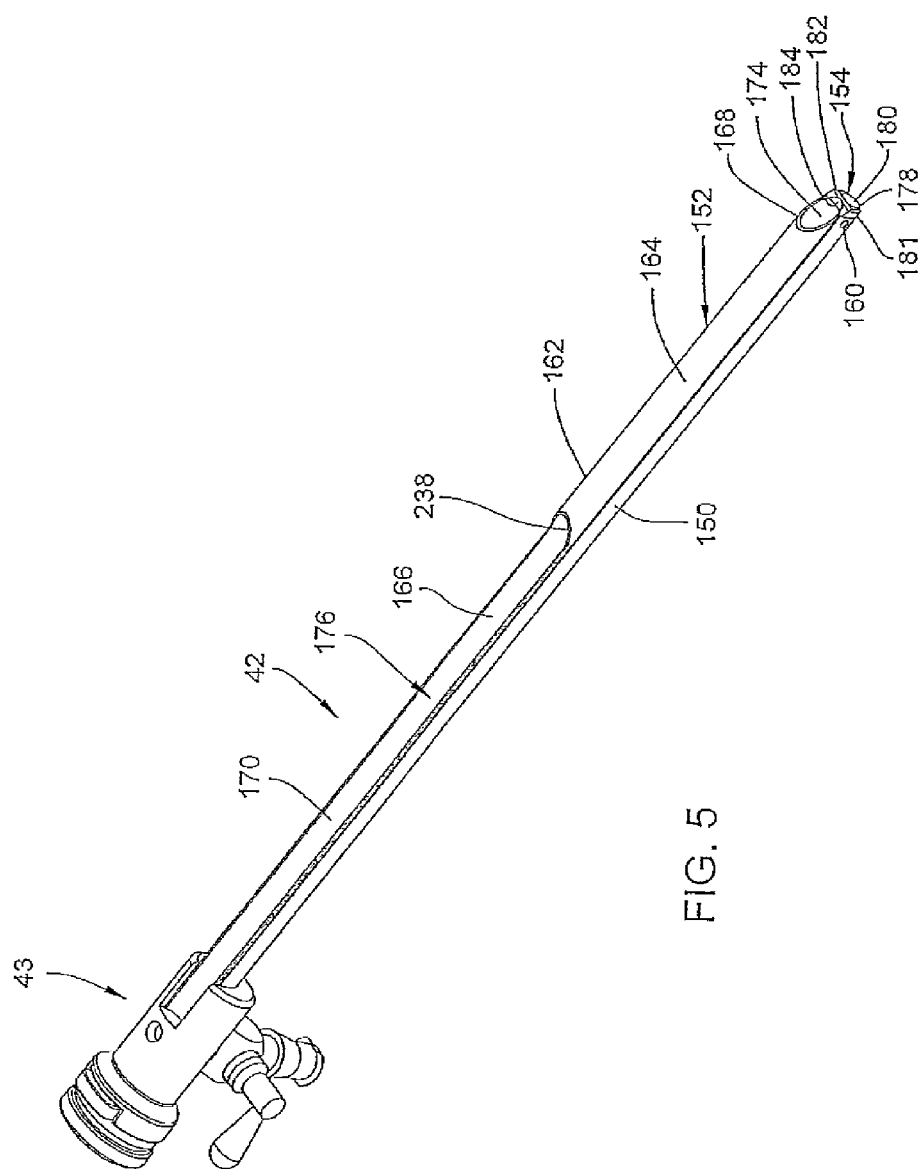
FIG. 5 is a perspective view of the access and positioning arrangement of the invention with a sheath lock.

In the illustrated example, the cannula assembly (see FIGS. 5-7) is configured to accept a portion of the endoscope 11 and the surgical instrument 12 therethrough. The cannula assembly 42 includes a full length bottom U-shaped member 150, a slotted top member 152 and an end cap 154 for the full length bottom U-shaped member 150. The full length bottom U-shaped member 150 includes a bottom arcuate wall 156 and a pair of parallel upper walls 158 that extend along an entire length of the cannula assembly 42 between the hub 43 and the end cap 154. A distal end of the full length bottom U-shaped member 150 includes a pair of co-linear distal end openings 160 extending through the pair of parallel upper walls 158 adjacent the end cap 154. The slotted top member 152 comprises a slotted tubular member 162 having a distal tubular portion 164 and a proximal slotted portion 166. The distal tubular portion 164 is cylindrical with a chamfered end 168. The proximal slotted portion 166 is semi-cylindrical forming a half-circle along the extent thereof, such that the proximal slotted portion 166 has a radially upwardly extending opening 170. As illustrated in FIGS. 6 and 7, the slotted top member 152 is fixed to the full length bottom U-shaped member 150 to form a fully enclosed lower chamber 172. The fully enclosed lower chamber 172 is defined by a bottom of the slotted top member 152 and the full length bottom U-shaped member 150. The slotted top member 152 and the full length bottom U-shaped member 150 also form a fully enclosed distal upper chamber 174 (FIG. 7) and a radially open proximal upper chamber 176 (FIG. 6). The end cap 154 includes a front wall 178 having a circular hole 180 therethrough, a U-shaped side wall 181 substantially conforming to the shape of the full length bottom U-shaped member 150 and connected to an end thereof, and a top wall 182 having a channel 184 on a top surface thereof as to not interfere with a distal end of the fully enclosed distal upper chamber 174. The sheath lock 44 partially encloses a proximal end of the fully enclosed distal upper chamber 174.

Figure 8:
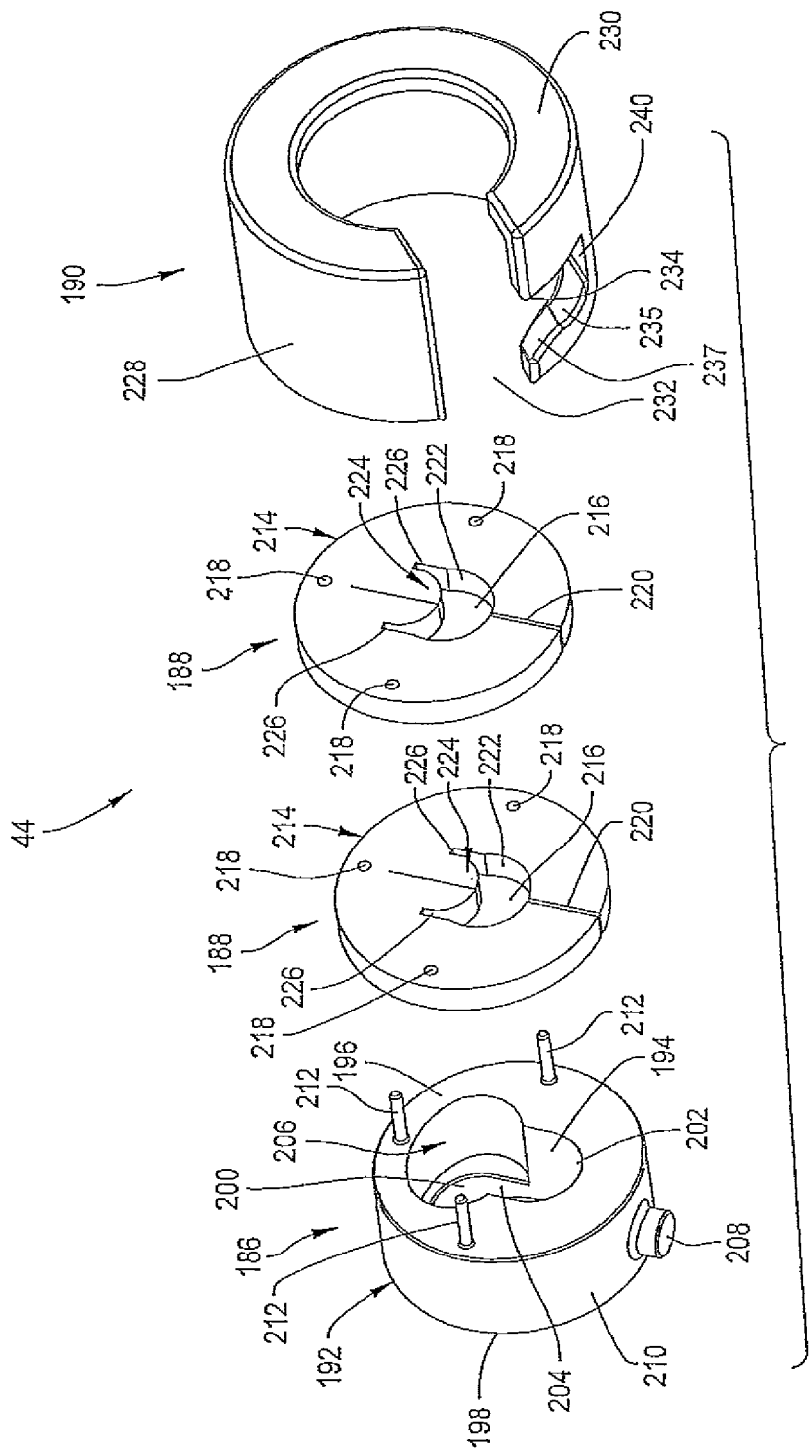
FIG. 8 is an exploded rear perspective view of the sheath lock of the access and positioning arrangement of the invention.
Figure 9:
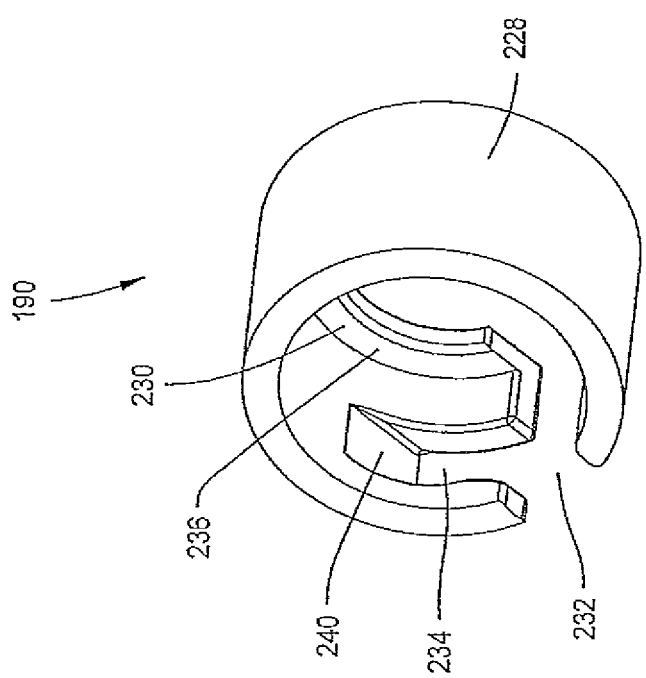
FIG. 9 is a front perspective view of a lock cap of the sheath lock of the access and positioning arrangement of the invention.

The illustrated sheath lock 44 (FIG. 8) is connected to the cannula assembly 42 and can be used to maintain a fluid within the fully enclosed distal upper chamber 174 defined between the slotted top member 152 and the full length bottom U-shaped member 150. The sheath lock 44 includes a distal fixed housing 186, a pair of disc seals 188 and a removable C-shaped lock cap 190 (FIGS. 8-9). The distal fixed housing 186 is fixedly connected to the cannula assembly 42. The distal fixed housing 186 includes a disc-shaped body 192 having an axially extending oval opening 194 passing from a proximal face 196 thereof to a distal face 198 thereof. The axially extending oval opening 194 is defined by a top semi-circular wall 200, a bottom semi-circular wall 202 and a pair of parallel side walls 204 extending between the top semi-circular wall 200 and the bottom semi-circular wall 202. An enlarged oval seal flap receiving space 206 having a major axis substantially perpendicular to the major axis of the axially extending oval opening 194 extends into the disc-shaped body 192 from the proximal face 196 thereof. The enlarged oval seal flap receiving space 206 extends only partially through the disc-shaped body 192 and receives a top portion of the axially extending oval opening 194 therein. A cylindrical lock pin 208 extends radially from an outer cylindrical surface 210 of the disc-shaped body 192. As discussed in more detail below, the cylindrical lock pin 208 assists in locking the removable C-shaped lock cap 190 and the disc seals 188 to the distal fixed housing 186 and the cannula assembly 42. A plurality of parallel alignment posts 212 extend proximally and perpendicularly from the proximal face 196 of the disc-shaped body 192. The parallel alignment posts 212 assist in properly aligning the pair of disc seals 188 in the sheath lock 44.

In the illustrated example, the disc seals 188 of the sheath lock 44 maintain a fluid within the fully enclosed distal upper chamber 174 defined between the slotted top member 152 and the full length bottom U-shaped member 150. Each disc seal 188 includes a flexible disc body 214 having a cannula opening 216, a plurality of alignment openings 218, and a radial slit 220. The cannula opening 216 is substantially U-shaped and includes a periphery 222 corresponding to an outside periphery of the cannula assembly 42 as illustrated in FIG. 6, including an outside shape of the full length bottom U-shaped member 150 and the proximal slotted portion 166 of the slotted top member 152. The radial slit 220 passes through the alignment openings 218 and bisects a U-shaped bisected flap 224 defined between top legs 226 of the alignment openings 218. The alignment openings 218 are configured to receive the parallel alignment posts 212 of the distal fixed housing 186 therein. Accordingly, the alignment openings 218 have the same relative spacing as the relative spacing between the parallel alignment posts 212 of the distal fixed housing 186. While three parallel alignment posts 212 and three corresponding alignment openings 218 are shown in FIG. 8, any number of alignment posts 212 and corresponding alignment openings 218 could be used (including only one alignment post 212 and one alignment opening 218). Furthermore, while two disc seals 188 are illustrated, any number of disc seals 188 (including only one) could be used. The removable C-shaped lock cap 190 maintains the pair of disc seals 188 in engagement with the distal fixed housing 186.

The illustrated removable C-shaped lock cap 190 is removably connected to the distal fixed housing 186 and maintains the disc seals 188 on the cannula assembly 42. The removable C-shaped lock cap 190 includes a slotted tubular outer wall 228 and a C-shaped proximal wall 230 connected to a proximal edge of the slotted tubular outer wall 228. The slotted tubular outer wall 228 and the C-shaped proximal wall 230 have an axially directed slot 232 extending therethrough. A lock niche 234 extends perpendicularly from the axially directed slot 232 into the slotted tubular outer wall 228, with a curved holding recess 235 being located on a distal side edge 237 of the lock niche 234. A distal surface of the C-shaped proximal wall 230 defines an abutment face 236 configured to abut and compress the disc seals 188 to maintain the disc seals 188 in position within the sheath lock 44.

The sheath lock 44 retards fluids from exiting the fully enclosed distal upper chamber 174 of the cannula assembly 42. In use, the sheath lock 44 is connected to the cannula assembly 42 by sliding the distal fixed housing 186 onto the cannula assembly 42 from the distal end of the cannula assembly 42, with the flap receiving space 206 being located over the distal tubular portion 164 of the slotted tubular member 162 and facing in a proximal direction. The distal fixed housing 186 is slid along the distal tubular portion 164 of the slotted tubular member 162 to a junction edge 238 between the distal tubular portion 164 and the proximal slotted portion 166 of the slotted tubular member 162. At that point, the distal fixed housing 186 is fixed in position to thereby surround a proximal end of the fully enclosed distal upper chamber 174 within the distal tubular portion 164 of the slotted tubular member 162. The distal fixed housing 186 can be fixed to the cannula assembly 42 by welding, adhesive or in any other manner.

Thereafter, the disc seals 188 are inserted over the cannula assembly 42 by moving the disc seals 188 in a radially inward direction over the cannula assembly 42 and by inserting the proximal slotted portion 166 of the slotted tubular member 162 and a proximal portion of the full length bottom U-shaped member 150 through the radial slit 220 in the disc body 214 of the disc seals 188 until the proximal slotted portion 166 of the slotted tubular member 162 and the proximal portion of the full length bottom U-shaped member 150 are fully located within the cannula opening 216 in the disc seals 188. The disc seals 188 are then slid axially in a distal direction towards the distal fixed housing 186 until the alignment posts 212 extending from the distal fixed housing 186 are fully inserted into the alignment openings 218 in the disc seals 188.

Finally, the removable C-shaped lock cap 190 is inserted over the cannula assembly 42 by moving the removable C-shaped lock cap 190 in a radially inward direction over the cannula assembly 42. Accordingly, the proximal slotted portion 166 of the slotted tubular member 162 and the proximal portion of the full length bottom U-shaped member 150 are inserted through the axially directed slot 232 in the removable C-shaped lock cap 190 until the proximal slotted portion 166 of the slotted tubular member 162 and the proximal portion of the full length bottom U-shaped member 150 are fully located within the center of the slotted tubular outer wall 228 of the removable C-shaped lock cap 190. The removable C-shaped lock cap 190 is then slid axially in a distal direction towards the distal fixed housing 186 and the disc seals 188 until the lock pin 208 extending radially from the distal fixed housing 186 is slid partially through the axially directed slot 232 in the removable C-shaped lock cap 190. As the removable C-shaped lock cap 190 is moved towards the distal fixed housing 186, the disc seals 188 will be compressed slightly between the proximal face 196 of the disc-shaped body 192 of the distal fixed housing 186 and the abutment face 236 of the C-shaped proximal wall 230 of the removable C-shaped lock cap 190. When the lock pin 208 extending radially from the distal fixed housing 186 is aligned with the lock niche 234 in the slotted tubular outer wall 228 of the removable C-shaped lock cap 190, the removable C-shaped lock cap 190 is rotated about a center longitudinal axis of the cannula assembly 42 until the lock pin 208 abuts an end wall 240 of the lock niche 234 and rests in the curved holding recess 235. The compression of the disc seals 188 will prevent the lock pin 208 from freely rotating to an open position and will prevent the lock pin 208 from moving out of the curved holding recess 235 in the lock niche 234.

To remove the disc seals 188 and the removable C-shaped lock cap 190, the removable C-shaped lock cap 190 is pushed towards the distal fixed housing 186 to compress the disc seals 188 and then rotated to move the lock pin 208 of the distal fixed housing 186 out of the curved holding recess 235 and out of the lock niche 234. The removable C-shaped lock cap 190 is then moved axially in a proximal direction to clear the disc seals 188 and moved radially away from the cannula assembly 42. The disc seals 188 can be removed in a similar fashion. As discussed in more detail below, the sheath lock 42 prevents fluid from exiting the fully enclosed distal upper chamber 174 of the cannula assembly 42 as the obturator 26 or the surgical instrument 12 is removed from the fully enclosed distal upper chamber 174.

To begin a surgical procedural, a puncture is made through the patient's skin at the surgical site with a scalpel or other suitable tool, and the distal end of the surgical tool arrangement 10 is inserted through the puncture and into the surgical site. During surgery, the surgical tool arrangement 10 typically includes the endoscope 11, the surgical instrument 12, and the access and positioning arrangement 14. However, the access and positioning arrangement 14 without the endoscope 11 and/or the surgical instrument 12 connected thereto is typically inserted into the puncture. When the access and positioning arrangement 14 does not have the endoscope 11 and/or the surgical instrument 12 connected thereto, another item is typically used in place of the endoscope 11 and/or the surgical instrument 12 during insertion of the access and positioning arrangement 14 into the patient. For example, the trocar 62 or the obturator 26 could be used in order to block fluid flow in a proximal direction through the cannula assembly 42.

FIG. 11 illustrates the trocar 62 located within the access and positioning arrangement 14 in the place of the endoscope 11. The trocar 62 includes an elongate rod 242 snugly axially slidable into the head central passage 48 of the hub 43 and through the fully enclosed lower chamber 172 of the cannula assembly 42. The trocar 62 further includes a proximal portion 244 coaxially fixed at a proximal end of the elongate rod 242. The proximal portion 244 includes a radially enlarged handgrip 246 for easily manipulating the trocar 62. The distal end of the trocar 62 is pointed as indicated in FIG. 11.

The illustrated trocar 62 is axially insertable into the access and positioning arrangement 14 in a distal direction to achieve the installed position shown in FIG. 11 to allow for protrusion of the distal end 248 of the trocar 62 distally from the distal end of the cannula assembly 42. This enables the trocar 62 to pierce patient tissue thereby allowing insertion of the distal end portion of the access and positioning arrangement 14 through patient tissue to an internal operating site (not shown). The trocar 62 can be locked to the access and positioning arrangement 14 in the same manner as the trocar is locked to the cannula in U.S. Pat. No. 5,456,673, and in the same manner as the endoscope 11 is locked to the access and positioning arrangement 14 as discussed in more detail below.

Figure 12:
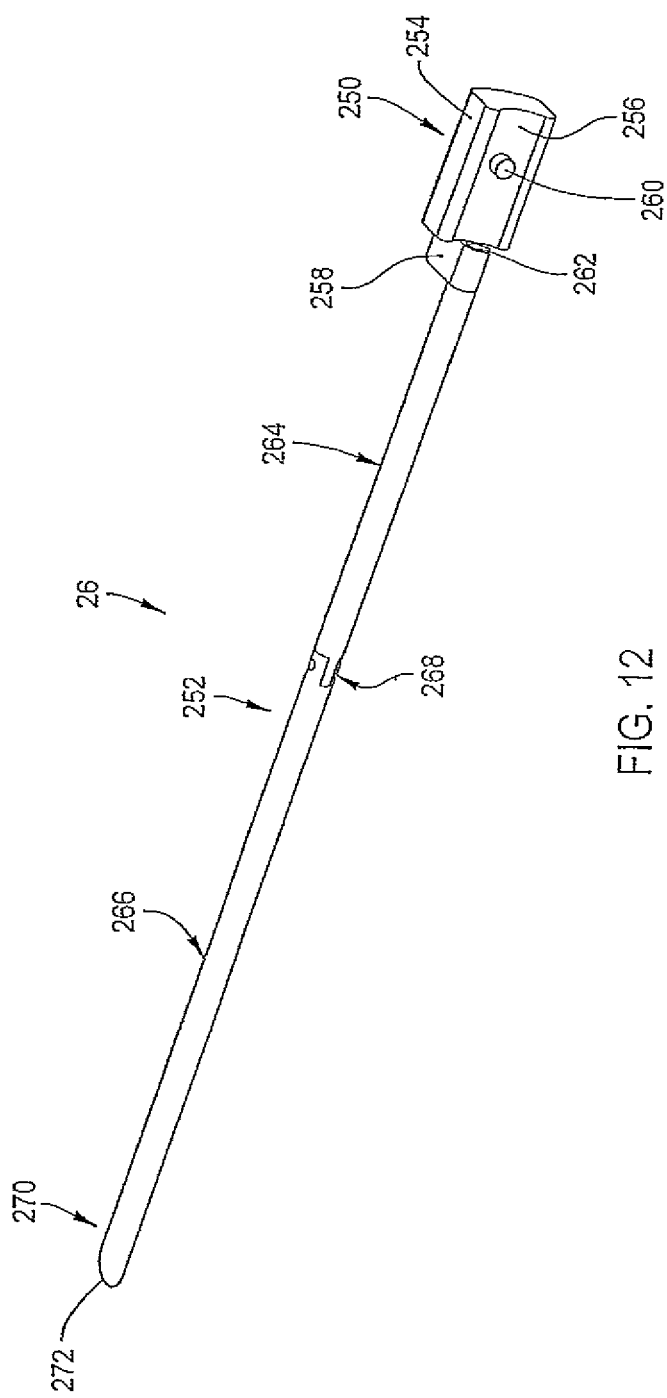
FIG. 12 is a bottom perspective view of the obturator for use with the access and positioning arrangement of the invention.

FIG. 11 illustrates the obturator 26 being located within the access and positioning arrangement 14 in the place of the surgical instrument 12. The obturator 26 (FIG. 12) includes a connection head 250 and an obturating arm 252. The connection head 250 is a block 254 having a concave curved lower surface 256 and a distal extension 258. The concave curved lower surface 256 has a centrally located dowel 260 extending radially therefrom. The distal extension 258 includes an opening 262 therethrough parallel with a center of curvature of the concave curved lower surface 256. The obturating arm 252 is connected to the connection head 250 by inserting a proximal end of the obturating arm 252 into the opening 262 in the distal extension 258 of the block 254. The obturating arm 252 includes a proximal portion 264 hingedly connected to a distal portion 266 at a pivoting joint 268. A distal end 270 of the distal portion 266 of the obturating arm 252 includes a blunt nose 272.

The illustrated obturator 26 is connected to the access and positioning arrangement 14 by first bending the obturating arm 252 at the pivoting joint 268 and placing the distal portion 266 of the obturating arm 252 into the radially open proximal upper chamber 176 of the cannula assembly 42 of the access and positioning arrangement 14. The distal portion 266 of the obturating arm 252 is then slid distally in an axial direction into the fully enclosed distal upper chamber 174 of the cannula assembly 42 of the access and positioning arrangement 14. During or after the sliding of the distal portion 266 of the obturating arm 252 into the fully enclosed distal upper chamber 174, the obturating arm 252 is pivoted about the pivoting joint 268 to bring the proximal portion 264 of the obturating arm 252 toward and into the radially open proximal upper chamber 176 of the cannula assembly 42 of the access and positioning arrangement 14. The connection head 250 of the obturator 26 will then engage the hub 43 of the access and positioning arrangement 14 by having the concave curved lower surface 256 of the block 254 of the connection head 250 of the obturator 26 abut an annular outer surface 274 of the distal head portion 46 of the hub 43 of the access and positioning arrangement 14. Furthermore, the centrally located dowel 260 extending radially from the concave curved lower surface 256 is inserted into a receiving bore 276 (see FIGS. 3 and 4) extending radially into a top of the distal head portion 46 of the hub 43 of the access and positioning arrangement 14, to axially fix the obturator 26 in position on the access and positioning arrangement 14.

The obturator 26 is similar to the trocar 62 except for having a blunt nose 272 instead of the point at the distal end 248 of the trocar 62. In a typical surgical sequence, the trocar 62 as described above is located in the fully enclosed lower chamber 172 of the cannula assembly 42 and a trocar identical to the obturator 26 discussed above except for having a point instead of the blunt nose 272 is located within the fully enclosed distal upper chamber 174 as the access and positioning arrangement 14 is inserted into the patient. Thereafter, the two trocars can be removed and an obturator identical to the trocar 62 discussed above except for having a blunt nose instead of the point is positioned in the fully enclosed lower chamber 172 of the cannula assembly 42 and the obturator 26 discussed above is positioned within the fully enclosed distal upper chamber 174 as the obturators may be useful in more gently parting tissue in the last stage of insertion of the access and positioning arrangement 14 into the surgical site. Nevertheless, it is contemplated that only the trocars or only the obturators (or any combination thereof) could be used during the full insertion of the access and positioning arrangement 14.

Once the access and positioning arrangement 14 is fully inserted into the patient, the obturator(s) and/or the trocar(s) are removed from the access and positioning arrangement 14 and the endoscope 11 and/or the surgical instrument 12 can be inserted into the access and positioning arrangement 14. At this juncture, the surgeon typically conducts a diagnostic "tour" with the endoscope 11 in order to view the surgical site. As the surgical instrument 12, the obturator 26 and/or a trocar are removed from the fully enclosed distal upper chamber 174 of the cannula assembly 42 of the access and positioning arrangement 14, the sheath lock 44 prevents fluid from exiting through a proximal end of the fully enclosed distal upper chamber 174. As the surgical instrument 12, the obturator 26 or a trocar are inserted into the fully enclosed distal upper chamber 174, the distal end of the surgical instrument 12, the obturator 26 or a trocar push against the U-shaped bisected flap 224 of the disc seals 188 to split the U-shaped bisected flap 224 into two parts and push the two parts of the U-shaped bisected flap 224 into the flap receiving space 206 in the distal fixed housing 186 of the sheath lock 44. As the surgical instrument 12, the obturator 26 or are trocar are removed from the fully enclosed distal upper chamber 174 of the cannula assembly 42 of the access and positioning arrangement 14, the two parts of the U-shaped bisected flap 224 will move back towards each other to thereby substantially block fluid from exiting the fully enclosed distal upper chamber 174 at a proximal end thereof. It is contemplated that the disc seals 188 can be removed and replaced as discussed above after each surgical procedure.

It is contemplated that the access and positioning arrangement 14 could be inserted into the incision with only the obturator 26 and the endoscope 11 positioned therein. In such a situation, the blunt nose 272 of the obturator 26 can be located immediately adjacent the distal end 18 of the endoscope 11 so that the chamfered distal ends of the obturator 26 and the endoscope 11 together define an essentially continuous chamfered distal tool edge which can be utilized to enlarge the incision.

Once the surgical instrument 12 and the endoscope 11 are positioned within the access and positioning arrangement 14 and the surgical tool arrangement 10 is in the proper position within the patient, the distal end of elongated outer tube 31 of surgical instrument 12 is then positioned within the field of view of the endoscope 11. In this regard, the distal end 18 of the endoscope 11 has a field of view of approximately 80-120 degrees, which is the total included angle centered on the direction of view of the endoscope 11, which direction of view is perpendicular to the plane of the distal end 18 of the endoscope 11 that is chamfered. The distal end 18 with a chamfer must face at least partially towards the distal end of the surgical instrument 12 at the surgical site, so that the surgical instrument 12 will be positioned within the field of view of the endoscope 11. The working or distal end of the surgical instrument 12 must be positioned within this defined field of view of the endoscope 11 in order for the surgeon to be able to properly view the operation of surgical instrument 12 at the surgical site. The defined position of the fully enclosed distal upper chamber 174 of the cannula member 42 of the access and positioning arrangement 14 relative to the endoscope 11, the position of which endoscope 11 is fixed via being locked within the hub 43 of the access and positioning arrangement 14 as discussed below, allows the surgeon to readily and easily insert the surgical instrument 12 via the fully enclosed distal upper chamber 174 into the surgical site and directly into the field of view of the endoscope 11. Once the surgical instrument 12 is positioned within access and positioning arrangement 14 and in the field of view of the endoscope 11, various operations can be carried out at the surgical site as needed. When a shaver is used as the surgical instrument 12, the rotational position of elongated outer tube 31 of the surgical instrument 12 can be varied as necessary within the fully enclosed distal upper chamber 174 by manipulating the handpiece within which hub 30 is mounted, which will effectively change the rotational position of the cutting window 33 of the elongated outer tube 31 at the surgical site.

During surgery, a conventional inflation gas source, a conventional suction source, or another desired fluid source, such as a source of irrigation liquid, can be sent from the valve unit 52, through the access and positioning arrangement 14, and into the surgical site. The fluid path extends from the source of such fluid, through the central fluid path 76 of the valve unit 52 (when the valve 84 is turned to an on position), into the branch tube 72 in the hub 43, through the T-shaped fluid path 69 and into the cannula assembly 42. The internal O-ring seal 82 within the hub 43 prevents the fluid from moving in a proximal direction past the internal O-ring seal 82. The fluid moving in the distal direction passes through the T-shaped fluid path 69 and into the head central passage 48 and into a proximal end of the fully enclosed lower chamber 172 of the cannula assembly 42. As illustrated in FIGS. 6 and 7, the fluid can pass through the fully enclosed lower chamber 172 of the cannula assembly 42 through a pair of fluid paths 201, with each fluid path 201 being located between one of the side surfaces of the endoscope 11, one of the parallel upper walls 158 of the full length bottom U-shaped member 150 and a half of a lower surface of the slotted top member 152. Once the fluid reaches the distal end of the fully enclosed lower chamber 172 of the cannula assembly 42, the front wall 178 of the end cap 154 of the cannula assembly 42 will divert the fluid radially through the distal end openings 160 in the full length bottom U-shaped member 150 of the cannula assembly 42.

It will also be contemplated that the pair of fluid paths 201 in the fully enclosed lower chamber 172 of the cannula assembly 42 could be sealed apart from each other by the endoscope 11 and that the access and positioning arrangement 14 may alternatively include multiple fluid ports through the valve unit 52, instead of just one fluid port. Specifically, the valve unit 52 may include a fluid inflow port and a fluid outflow port, as well as a suitable valve arrangement to allow control of such ports. Such an arrangement is conventional and allows the surgeon to both deliver fluid to the surgical site as well as remove fluid from the surgical site via the access and positioning arrangement 14, to thereby maintain a desirable fluid pressure at the surgical site. In such a situation, the hub 43 would also include separate fluid paths therethrough divided by the endoscope 11 and with a radially extending wall extending through the branch tube 72 to keep the paths separate.

Figure 2:
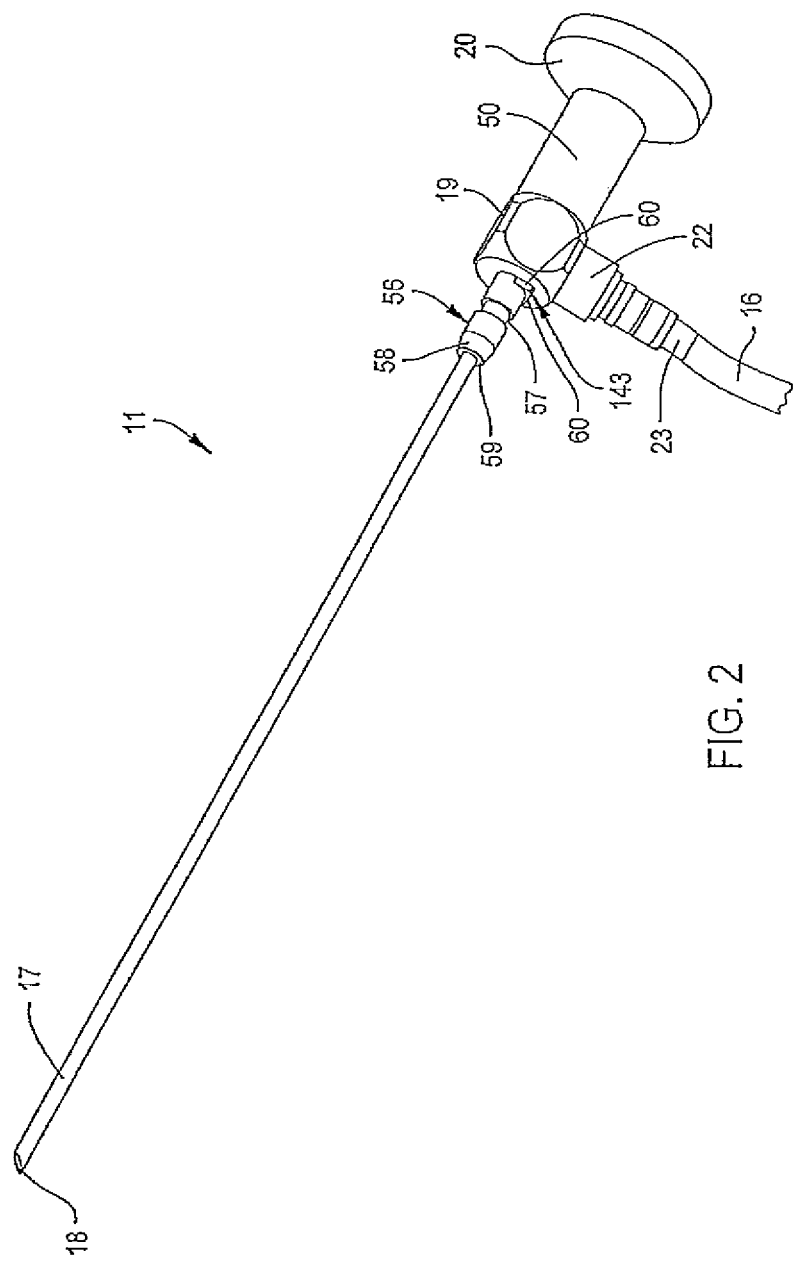
FIG. 2 is a perspective view of an endoscope for use with the access and positioning arrangement of the invention.

As the illustrated endoscope 11 is inserted into the access and positioning arrangement 14, the endoscope 11 is configured to be locked into the proximal head portion 80 of the hub 43. As illustrated in FIG. 2, the proximal end 19 of the endoscope 11 includes a distal end cylinder 50 and a generally cylindrical intermediate diameter portion 56 at a distal end of the distal end cylinder 50, with the generally cylindrical intermediate diameter portion 56 having an annular lock groove 57 therein between the ends thereof. The distal end of the generally cylindrical intermediate diameter portion 56 includes a taper 58 extending downward toward a top of the hollow shaft 17, which extends distally out of the generally cylindrical intermediate diameter portion 56.

In the illustrated example, the endoscope 11 is locked to the hub 43 as the hollow shaft 17 of the endoscope 11 is inserted into a proximal end of the hub 43 and through the head central passage 48 of the hub 43 as disclosed in U.S. Pat. No. 5,456,673. First, the distal end 18 of the endoscope 11 can be led downward past the annular cap 91B and into the upper portion 40 of the head central passage 48. The distal end 18 of the endoscope 11 clears the internal O-ring seal 82 easily as it passes downward therethrough, so as not to damage the internal O-ring seal 82. The downward tapered portion 41 guides the distal end 18 of the endoscope into the narrow portion 65 of the head central passage 48 and thence down into the cannula assembly 42.

Continued insertion of the illustrated endoscope 11 into the hub 43 brings the taper 58 forward close to the proximal end of the upper portion 40 of the head central passage 48. Continued movement of the endoscope 11 passes the taper 58 down into the annular cap 91B and through an oblong hole 120 in the generally rectangular slider 110. The taper 58 engages a slider bevel 124 of the generally rectangular slider 110 and cams the generally rectangular slider 110 laterally against the circumferential tension of the resilient O-ring 130, thereby stretching the O-ring 130 as a slider post 115 of the generally rectangular slider 110 moves to an unlocked position. Continued movement of the endoscope 11 moves the distal portion of the generally cylindrical intermediate diameter portion 56 below the annular lock groove 57 into downward sliding contact with an end 123 of the oblong hole 120 opposite the slider post 115, to hold the generally rectangular slider 110 in the unlock position.

The illustrated taper 58 continues downward into engagement with the internal O-ring seal 82. A rounded bottom end 59 of the taper 58 prevents the taper 58 from injuring the internal O-ring seal 82 as the taper 58 passes therein. Continued downward movement of the taper 58 past the internal O-ring seal 82 presses the internal O-ring seal 82 radially outward to bring the generally cylindrical intermediate diameter portion 56 of the endoscope 11 into sealing contact with the internal O-ring seal 82, pressing the internal O-ring seal 82 radially outward against the surrounding material of the annular pedestal 91A.

As the generally cylindrical intermediate diameter portion 56 of the endoscope 11 moves down past the generally rectangular slider 110, the annular lock groove 57 of the endoscope 11, due to the reduced diameter, allows the O-ring 130 to resiliently pull the slider 110 back to the lock position, wherein the end 123 of the oblong hole 120 enters the annular lock groove 57 and overlies the generally cylindrical intermediate diameter portion 56 of the endoscope 11 to positively mechanically block movement of the endoscope 11 out of the hub 43. In the embodiment shown, the proximal end 19 of the endoscope 11 comes to rest upon the top of the annular cap 91B as the generally cylindrical intermediate diameter portion 56 of the endoscope 11 drops slightly below the generally rectangular slider 110. The endoscope 11 is thus fully installed in a use position within the hub 43. The trocar 62 and the obturator can also be locked to the hub 43 in the same manner.

When the endoscope 11 is in a fully inserted, locked, position in the access and positioning arrangement 14, the internal O-ring seal 82 is radially pressed between the generally cylindrical intermediate diameter portion 56 of the endoscope 11 and the radially outer wall of the annular groove 81 in the annular pedestal 91A, which provides a tight fluid pressure seal between the endoscope 11 and access and positioning arrangement 14 to prevent upward loss therepast of fluid, such as pressure gas, from the operating site in which the distal end of the access and positioning arrangement 14 is located.

To remove the endoscope 11 from the hub 43 requires a reversal of the above described installation process. Removal of the endoscope 11 is initiated by pulling the endoscope 11 out of the hub 43, while pressing against a manually pushable end 114 of the generally rectangular slider 110 to shift the slider 110 against the resilient force of the O-ring 130 beyond its unlocked position. With the generally rectangular slider 110 moved, the generally rectangular slider 110 clears the top of the generally cylindrical intermediate diameter portion 56 of the endoscope 11, allowing the endoscope 11 to be pulled out of the hub 43.

Figure 10:
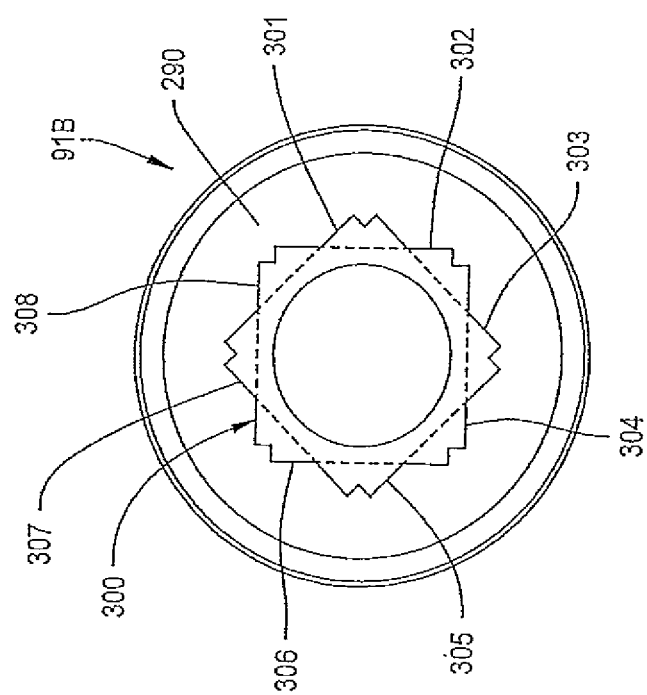
FIG. 10 is an end view of an annular cap of the hub of the access and positioning arrangement of the invention.

In the illustrated example, a proximal end of the generally cylindrical intermediate diameter portion 56 can include a radially protruding, plate-like key 143, with the key 143 being connected to a distal end surface of the distal end cylinder 50. The key 143 can include edges 60 forming a rectangle. The edges 60 of the key 143 can be used to orient the endoscope 11 in a selected rotational position within the hub 43 of the access and positioning arrangement 14. As illustrated in FIGS. 4 and 10, a proximal end face 290 of the annular cap 91B includes a non-circular cut-out 300 configured to accept the key 143 therein. In the illustrated example, the non-circular cut-out 300 forms eight pairs of co-planar walls, with each pair of co-planar walls defining an abutment and alignment surface 301-308. As the endoscope 11 is inserted into the hub 43 of the access and positioning arrangement 14, the key 143 allows the endoscope 11 to be located in one of eight angular positions because the abutment and alignment surfaces 301-308 within the non-circular cut-out 300 in the proximal end face 290 of the annular cap 91B will only allow the edges 60 of the key 143 to be located against one of the abutment and alignment surfaces 301-308. With eight abutment and alignment surfaces 301-308, the endoscope 11 can be positioned in orientations offset by 45°. While eight abutment and alignment surfaces 301-308 are illustrated, it is contemplated that the key 143 could have any number of edges 60 and the non-circular cut-out 300 could have any number of abutment and alignment surfaces 301-308 to limit the angular orientation of the endoscope 11. For example, the non-circular cut-out 300 could have two or three abutment and alignment surfaces to limit the endoscope 11 to two or three positions, respectfully.

Figure 13:
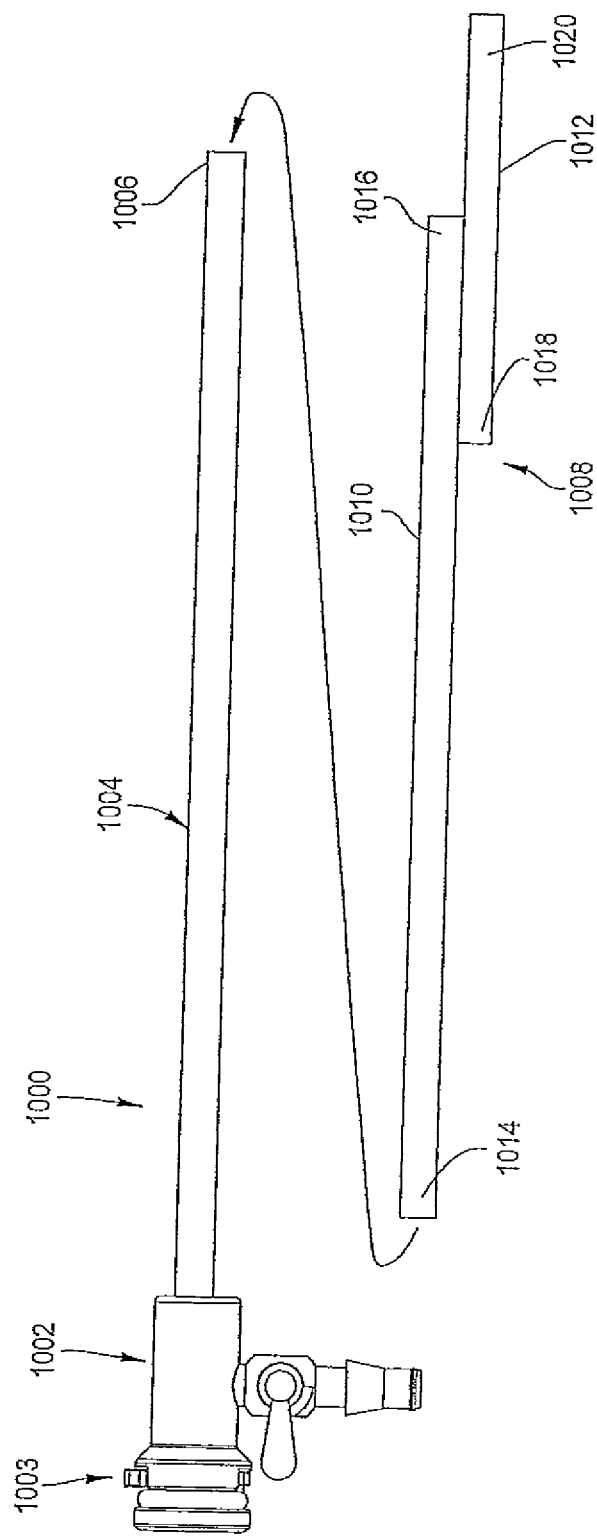
FIG. 13 is an exploded side view of a second embodiment of the access and positioning arrangement of the invention.

The reference numeral 1000 (FIG. 13) generally designates another embodiment of the present invention, having a second embodiment for the access and positioning arrangement. The second embodiment of the access and positioning arrangement 1000 includes substantially the same hub 1002 (including the locking arrangement in the lock unit 1003), except that the U-shaped slot of the hub 1002 does not include an open U-shaped slot. The U-shaped slot is closed at the top. The cannula assembly includes a first tube 1004 substantially corresponding to the fully enclosed lower chamber 172 of the first embodiment, except that a proximal end 1014 of a lower chamber tube 1010 of a double tube assembly 1008 is inserted into a distal end 1006 of the first tube 1004 to fully form the fully enclosed lower chamber 172. The fully enclosed distal upper chamber 174 is located within an upper chamber tube 1012 of the double tube assembly 1008 having an outer circumferential edge connected to a distal end 1016 of the lower chamber tube 1010. An endoscope (or obturator or trocar) can be inserted through the hub 1002, through the first tube 1004 and through the lower chamber tube 1010 of the double tube assembly 1008 to extend out of the distal end 1016 of the lower chamber tube 1010 of the double tube 1008. The surgical instrument (or obturator or trocar) can be inserted into a proximal end 1018 of the upper chamber tube 1012 of the double tube assembly 1008 and out the distal end 1020 of the upper chamber tube 1012 of the double tube assembly 1008 to be used as described above.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An access and positioning arrangement for use in an endoscopic surgical procedure in which first and second surgical tools are utilized, said arrangement comprising:
    a hub having a head central passage therethrough, the hub being configured to receive the first surgical tool therein with the first surgical tool extending through the head central passage; and
    a cannula assembly connected to the hub;
    the cannula assembly defining a first fully enclosed chamber extending substantially along a length of the cannula assembly, the first fully enclosed chamber being coextensive with the head central passage such that the first surgical tool is configured to extend through the hub and the first fully enclosed chamber and to a distal end of the cannula assembly;
    the cannula assembly defining a second fully enclosed chamber that extends along only a portion of the length of the cannula assembly and spaced from the hub, the second fully enclosed chamber having an entrance and an exit, with the entrance and the exit being spaced from the hub for allowing the second surgical tool to extend through the second fully enclosed chamber without also passing through the hub or the first fully enclosed chamber;
    the first fully enclosed chamber and the second fully enclosed chamber being substantially parallel such that the first surgical tool and the second surgical tool can extend substantially in parallel from the distal end of the cannula assembly;
    the cannula assembly further including a semi-circular member;
    the second fully enclosed chamber being circular; and
    the semi-circular member having a center of curvature co-linear with a central longitudinal axis of the second fully enclosed chamber.

2. The access and positioning arrangement of claim 1, wherein: the first fully enclosed chamber is non-circular.

3. The access and positioning arrangement of claim 2, wherein:
    the hub includes a valve unit connected thereto, with a fluid path extending through the hub and into the first fully enclosed chamber, the fluid path exiting the first fully enclosed chamber through at least one opening adjacent but spaced from the distal end of the cannula assembly.

4. The access and positioning arrangement of claim 1, wherein: a seal covers the entrance of the second fully enclosed chamber.

5. The access and positioning arrangement of claim 4, wherein:
    the seal comprises a fixed member fixed to the cannula assembly at the entrance of the second fully enclosed chamber, a removable lock cap configured to be removably connected to the fixed member, and at least one removable seal disk having a bifurcated flap covering the entrance to the second fully enclosed chamber and configured to be trapped between the fixed member and the removable lock cap.

6. The access and positioning arrangement of claim 1, wherein: the exit is beveled.

7. The access and positioning arrangement of claim 1, wherein: at least a portion of the distal end of the cannula is beveled.

8. The access and positioning arrangement of claim 1, further including:
    an obturator having a head and an arm extending from the head, the arm having a first proximal portion fixed to the head and pivotally connected to a second distal portion;
    wherein the obturator is configured to be connected to the hub with a mating pin and slot connector assembly, with the first proximal portion of the arm being located in the semi-circular member and the second distal portion being located in the second fully enclosed chamber.

9. An access and positioning arrangement for use in an endoscopic surgical procedure in which first and second surgical tools are utilized, said arrangement comprising:
    a hub having a head central passage therethrough, the hub being configured to receive the first surgical tool therein with the first surgical tool extending through the head central passage; and
    a cannula assembly connected to the hub;
    the cannula assembly defining a first fully enclosed chamber extending substantially along a length of the cannula assembly, the first fully enclosed chamber being coextensive with the head central passage such that the first surgical tool is configured to extend through the hub and the first fully enclosed chamber and to a distal end of the cannula assembly;
    the cannula assembly defining a second fully enclosed chamber that extends along only a portion of the length of the cannula assembly and spaced from the hub, the second fully enclosed chamber having an entrance and an exit, with the entrance and the exit being spaced from the hub for allowing the second surgical tool to extend through the second fully enclosed chamber without also passing through the hub or the first fully enclosed chamber;
    the first fully enclosed chamber and the second fully enclosed chamber being substantially parallel such that the first surgical tool and the second surgical tool can extend substantially in parallel from the distal end of the cannula assembly;
    wherein the cannula assembly comprises a first tube connected to the hub and forming at least a first portion of the first fully enclosed chamber and a second tube assembly, the second tube assembly including a first tube member and a second tube member, the first tube member being located partially within the first tube and forming a second portion of the first fully enclosed chamber, the second tube member forming the second fully enclosed chamber.

10. An access and positioning arrangement for use in an endoscopic surgical procedure in which first and second surgical tools are utilized, said arrangement comprising:
a hub having a head central passage therethrough, the hub being configured to receive the first surgical tool therein with the first surgical tool extending through the head central passage; and
a cannula assembly connected to the hub;
the cannula assembly defining a first fully enclosed chamber extending substantially along a length of the cannula assembly, the first fully enclosed chamber being coextensive with the head central passage such that the first surgical tool is configured to extend through the hub and the first fully enclosed chamber and to a distal end of the cannula assembly;
the cannula assembly defining a second fully enclosed chamber that extends along only a portion of the length of the cannula assembly and spaced from the hub, the second fully enclosed chamber having an entrance and an exit, with the entrance and the exit being spaced from the hub for allowing the second surgical tool to extend through the second fully enclosed chamber without also passing through the hub or the first fully enclosed chamber;
the first fully enclosed chamber and the second fully enclosed chamber being substantially parallel such that the first surgical tool and the second surgical tool can extend substantially in parallel from the distal end of the cannula assembly;
wherein the cannula assembly comprises a first U-shaped member and a second member having a first semi-circular open portion and a second circular closed portion, the second member being connected to a top of the first U-shaped member to define the first fully enclosed chamber, with the first fully enclosed chamber being non-circular, and the second circular closed portion of the second member forming the second fully enclosed chamber.

11. The access and positioning arrangement of claim 10, further including:
a seal assembly located at a juncture of the first semi-circular open portion and the second circular closed portion of the second member of the cannula assembly, the seal assembly being configured to retard fluid from leaving the second fully enclosed chamber through the entrance thereof.

12. An access and positioning arrangement for use in an endoscopic surgical procedure in which first and second surgical tools are utilized, said arrangement comprising:
a cannula assembly defining a first fully enclosed chamber extending substantially along a length of the cannula assembly, the first fully enclosed chamber being configured to accept the first surgical tool therethrough and to a distal end of the cannula assembly;
the cannula assembly defining a second fully enclosed chamber that extends along only a portion of the length of the cannula assembly, the second fully enclosed chamber having an entrance and an exit, with the entrance and the exit allowing the second surgical tool to extend through the second fully enclosed chamber without also passing through the first fully enclosed chamber;
the first fully enclosed chamber and the second fully enclosed chamber being substantially parallel such that the first surgical tool and the second surgical tool can extend substantially in parallel from the distal end of the cannula assembly;
the cannula assembly including a semi-circular member;
the second fully enclosed chamber being circular;
the semi-circular member having a center of curvature co-linear with a central longitudinal axis of the second fully enclosed chamber; and
an obturator having a head and an arm extending from the head, the arm having a first proximal portion fixed to the head and pivotally connected to a second distal portion;
wherein the obturator is configured to be engaged with the cannula assembly, with the first proximal portion of the arm being located in the semi-circular member and the second distal portion being located in the second fully enclosed chamber.

* * * * *